United States Patent [19]

Hiskey

[11] Patent Number: 5,395,945
[45] Date of Patent: Mar. 7, 1995

[54] SYNTHESIS OF 3,3-DINITROAZETIDINE

[75] Inventor: Michael A. Hiskey, Los Alamos, N. Mex.

[73] Assignee: The United States of America as represented by the United States Department of Energy, Washington, D.C.

[21] Appl. No.: 37,873

[22] Filed: Mar. 29, 1993

[51] Int. Cl.$^6$ ............................................. C07D 205/04
[52] U.S. Cl. ..................................................... 548/953
[58] Field of Search ........................................ 548/953

[56] References Cited

PUBLICATIONS

Hiskey et al., "Synthesis of 3,3–Dinitroazetidine from 1–t–Butyl–3,3–dinitroazetidine," J. Heterocyclic Chem., 29, vol. 29, pp. 1855–1856 (1992).
Archibald et al., "Synthesis and X–ray Crystal Structure of 1,3,3–Trinitroazetidine," J. Org. Chem., vol. 55, No. 9, pp. 2920–2924 (1990).
Yajima et al., "Trifluoromethanesulfphonic Acid, as a Deprotecting Reagent in Peptide Chemistry," J.C.S. Chem. Comm. pp. 107–108 (1974).
Hobson et al., "Cleavage of Tertiary Bases with Phenyl Chloroformate: The Reconversion of 21–Deoxyajmaline into Ajmaline," J. Chem. Soc. (C), pp. 2015–2017 (1967).
Glaser et al., "Stickstoff–Verbindungen II," (1957) p. 142.
Piotrowska et al., "Reactions of Nitroparaffins. Part XCVII* Novel Features of the Reaction of 2,2–Dinitropropanediol–1,3 with Primary Amines," Rocznike Chemii Ann. Soc. Chem. Polonorum 45, pp. 2107–2111 (1971).

*Primary Examiner*—Mary C. Lee
*Assistant Examiner*—Jacqueline Haley
*Attorney, Agent, or Firm*—Bruce H. Cottrell; William A. Eklund; William R. Moser

[57] ABSTRACT

The compound, 3,3-dinitroazetidine, and a process of preparing 3,3-dinitroazetidine including reacting a mixture of 1-tertiary-butyl-3,3-dinitroazetidine and benzyl chloroformate to form 1-(benzyloxycarbonyl)-3,3-dinitroazetidine, reacting the 1-(benzyloxycarbonyl)-3,3-dinitroazetidine and trifluoromethanesulfonic acid to form 3,3-dinitroazetidinium trifluoromethanesulfonate, and neutralizing the 3,3-dinitroazetidinium trifluoromethanesulfonate with a base to form 3,3-dinitroazetidine are provided. Salts of the 3,3-dinitroazetidine and preparation of such salts are also disclosed.

12 Claims, 1 Drawing Sheet

SYNTHESIS OF 3,3-DINITROAZETIDINE

FIELD OF THE INVENTION

The present invention relates to field of organic synthesis and more particularly to the synthesis of 3,3-dinitroazetidine and salts thereof.

BACKGROUND OF THE INVENTION

Since the synthesis of 1,3,3-trinitroazetidine (TNAZ) as a melt castable high performance explosive, the structurally related free base 3,3-dinitroazetidine, as well as the salts thereof, have been of interest. However, the salts and free base of 3,3-dinitroazetidine have not been sucessfully prepared.

A synthesis for the 3,3-dinitroazetidine has now been developed.

Accordingly, it is an object of the present invention to provide the compound 3,3-dinitroazetidine and a method of synthesizing 3,3-dinitroazetidine.

It is another object of the present invention to provide salts of the compound 3,3-dinitroazetidine and a method of preparing salts of 3,3-dinitroazetidine.

SUMMARY OF THE INVENTION

To achieve the foregoing and other objects, and in accordance with the purposes of the present invention, as embodied and broadly described herein, the present invention provides 3,3-dinitroazetidine and a process of preparing 3,3-dinitroazetidine including reacting a mixture of 1-tertiarybutyl-3,3-dinitroazetidine and a chloroformate to form a 1-(R-substituted oxycarbonyl)-3,3-dinitroazetidine, reacting the 1-(R-substituted oxycarbonyl)-3,3-dinitroazetidine and trifluoromethanesulfonic acid to form 3,3-dinitroazetidinium trifluoromethanesulfonate, and neutralizing the 3,3-dinitroazetidinium trifluoromethanesulfonate with a base to form 3,3-dinitroazetidine. Preferably, the chloroformate is benzyl chloroformate.

The present invention still further provides 3,3-dinitroazetidinium nitrate and a process of preparing 3,3-dinitroazetidinium nitrate including reacting 3,3-dinitroazetidinium trifluoromethanesulfonate with a nitrate salt to form 3,3-dinitroazetidinium nitrate.

The present invention also provides 3,3-dinitroazetidinium 3,5-dinitro-1,2,4-trizolate and a process of preparing 3,3-dinitroazetidinium 3,5-dinitro-1,2,4-triazolate including reacting 3,3-dinitroazetidinium trifluoromethanesulfonate with a dinitro-triazolate salt to form 3,3-dinitroazetidinium 3,5-dinitro-1,2,4-triazolate.

The present invention also provides di-(3,3-dinitroazetidinium) 4,4',5,5'-tetranitro-2,2'-bi-imidazolate and a process of preparing di-(3,3-dinitroazetidinium) 4,4',5,5'-tetranitro-2,2'-bi-imidazolate including reacting 3,3-dinitroazetidinium trifluoromethanesulfonate with a tetranitro-bi-imidazolate salt to form di-(3,3-dinitroazetidinium) 4,4',5,5'-tetranitro-2,2'-bi-imidazolate.

Still further, the present invention provides a process of preparing 1,3,3-trinitroazetidine including reacting a mixture of 1-tertiarybutyl-3,3-dinitroazetidine and a chloroformate to form a 1-(R-substituted oxycarbonyl)-3,3-dinitroazetidine where R is an alkyl or aryl group, reacting said 1-(R-substituted oxycarbonyl)-3,3-dinitroazetidine and trifluoromethanesulfonic acid to form 3,3-dinitroazetidinium trifluoromethanesulfonate, neutralizing said 3,3-dinitroazetidinium trifluoromethanesulfonate with a base to form 3,3-dinitroazetidine, admixing said 3,3-dinitroazetidine with ammonium nitrate in amounts sufficient to yield the energetic salt 3,3-dinitroazetidinium nitrate, and, dehydrating said 3,3-dinitroazetidinium nitrate to yield 1,3,3-trinitroazetidine.

DETAILED DESCRIPTION

Figure 1:
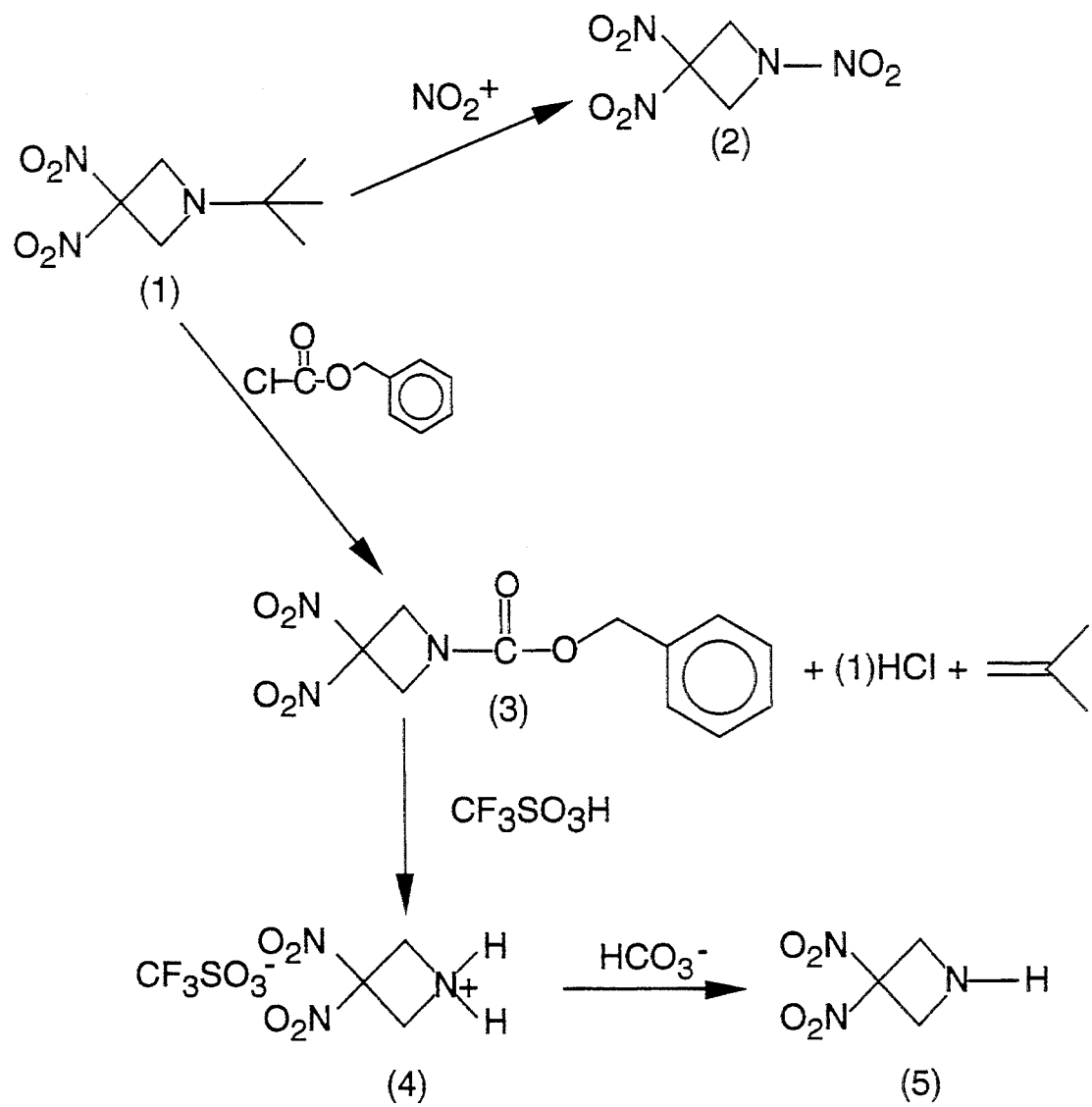
FIG. 1 illustrates the synthetic route of the present process of preparing 3,3-dinitroazetidine.

The present invention is concerned with the compound 3,3-dinitroazetidine and a method of synthesizing 3,3-dinitroazetidine. The present invention is also concerned with energetic salts of the compound 3,3-dinitroazetidine and methods for their preparation as well as a high-yield process for the preparation of 1,3,3-trinitroazetidine using 3,3-dinitroazetidine as a starting material.

In the present synthetic scheme for 3,3-dinitroazetidine, the initial precursor material is 1-tertiary-butyl-3,3-dinitroazetidine. This precursor material can be initially reacted with a chloroformate, e.g., benzyl chloroformate whereby isobutylene is formed, in an elimination reaction along with the formation of generally equimolar amounts of a carbamate, e.g., 1-(benzyloxycarbonyl)-3,3-dinitroazetidine, and 1-tertiary-butyl-3,3-dinitroazetidine hydrochloride. The resultant carbamate can then be reacted with, e.g., trifluoromethanesulfonic acid whereby the carbamate is cleaved to form 3,3-dinitroazetidinium trifluoromethanesulfonate. Neutralization of the 3,3-dinitroazetinium trifluoromethanesulfonate with a base can yield the compound 3,3-dinitroazetidine.

The chloroformate reacted with the 1-tertiary-butyl-3,3-dinitroazetidine can generally be any chloroformate, such as benzyl chloroformate, or an alkyl chloroformate such as methyl chloroformate. Preferably, the chloroformate is benzyl chloroformate or methyl chloroformate. Other electrophiles such as oxalylchloride and phosgene may also be reacted with the 1-tertiary-butyl-3,3-dinitroazetidine. The resultant product from the reaction of the 1-tertiary-butyl-3,3-dinitroazetidine with the chloroformate is a 1-(R-substituted oxycarbonyl)-3,3-dinitroazetidine wherein R is, e.g., an alkyl or aryl group.

The intermediate 3,3-dinitroazetidinium trifluoromethanesulfonate has been found to have a pKa of about 7.5. To obtain the free 3,3-dinitroazetidine product, neutralization of the 3,3-dinitroazetidinium trifluoromethanesulfonate intermediate material can generally be accomplished with bases such as sodium bicarbonate or sodium carbonate. Preferably, the base for neutralization is sodium bicarbonate.

The basicity of the 3,3-dinitroazetidine allows for the preparation of related energetic salts. Such energetic salts of the compound 3,3-dinitroazetidine can be formed by admixing the intermediate compound 3,3-dinitroazetidinium trifluoromethanesulfonate with a salt containing the desired anion species under suitable reaction conditions. For example, the 3,3-dinitroazetidinium trifluoromethanesulfonate can be admixed with salts such as nitrate salts, e.g., ammonium nitrate, nitrotriazolate salts, e.g., ammonium 3,5-dinitro-1,2,4-triazolate, or salts such as, e g., 4,4',5,5'-tetranitro-2,2'-bi-imidazolate, di-(3,3-dinitroazetidinium) 4,4',5,5'-tetranitro-2,2'-bi-imidazolate, 4,5-dinitroimidazolate, trinitroimidazolate, 2,4-dinitroimidazolate, 5,5'-dinitro-3,3'-bi(1,2,4-bitriazolate), 5-nitro-1,2,4-triazol-3-one, nitrotetrazolate, dinitramidic acid, picrate, trinitromethylate, or 3,5-dinitropyrazolate.

In another embodiment of the present invention, 3,3-dinitroazetidine can serve as a starting material for the preparation of 1,3,3-trinitroazetidine. After preparation of 3,3-dinitroazetidine, the material can be admixed with, e.g., ammonium nitrate to form the energetic salt, 3,3-dinitroazetidinium nitrate. This material can then be dehydrated to form the product 1,3,3-trinitroazetidine. This process is high yielding and produces a minimum of byproducts.

The present invention is more particularly described in the following examples which are intended as illustrative only, since numerous modifications and variations will be apparent to those skilled in the art.

All reagents were purchased from commercial sources except for 1-tertiary-butyl-3,3-dinitroazetidinium trifluoroacetate which was obtained from Fluorochem Inc., Azusa, Calif. NMR spectra were obtained on a JEOL GSX-270 spectrometer. Chemical shifts were determined relative to internal tetramethylsilane for $^1$H and $^{13}$C spectra. Melting points were determined at 2° per minute with a Metler FP1 apparatus.

EXAMPLE 1

To 1-tertiary-butyl-3,3-dinitroazetidine (20 g, 0.099 mole) in 25 milliliters (ml) of chloroform was added benzyl chloroformate (9.24 g, 0.054 mole). The mixture was stirred under reflux for 24 hours during which time isobutylene was generated and a white precipitate was formed. The mixture was allowed to cool and was the precipitate was separated by filtration. The filter cake was washed with methylene chloride, air dried and weighed to yield 6.4 g (27%) of 1-tertiary-butyl-3,3-dinitroazetidine hydrochloride. The filtrate was evaporated under vacuum to yield a yellow solid. This solid was taken up in warm toluene, the mixture filtered while hot, and the filtrate treated with hexanes to crystallize the product. The resultant product was collected by filtration and dried to give 7.3 g (26% yield) of pure 1-(benzyloxycarbonyl)-3,3-dinitroazetidine. The melting point of the product was 77.5°–78°. Later runs with longer reaction times between the 1-tertiary-butyl-3,3-dinitroazetidine and benzyl chloroformate in refluxing methylene chloride afforded higher yields.

Analysis $^1$H-nmr (deuteriochloroform): δ4.81 (s,4H), 5.16 (s,2H), 7.37 (s,5H); $^{13}$C-nmr (deuteriochloroform): δ58.1, 68.2, 128.3, 128.7, 135.2, 155.5. Anal. Calcd. for $C_{11}H_{11}N_3O_5$: C, 46.98; H, 3.94; N, 14.94. Found: C, 46.86; H, 4.34; N, 15.40.

EXAMPLE 2

To a solution of 1-(benzyloxycarbonyl)-3,3-dinitroazetidine (8.0 g, 0.028 mole) in 80 ml of methylene chloride containing anisole (9.24 g, 0.08 mole) was added trifluoromethanesulfonic acid (10 g, 0.067 mole), slowly with vigorous stirring at room temperature. Carbon dioxide was evolved and the solution turned light red in color. Stirring was continued for about 30 minutes after the addition. Diethyl ether was added slowly to quench the reaction and precipitate the resultant product. The solids were filtered, washed with diethyl ether and air-dried to give 4.10 g (97% yield) of pure 3,3-dinitroazetidinium trifluoromethanesulfonate. The melting point of the product was 176° (dec.).

Analysis $^1$H-nmr (deuteriomethyl sulfoxide): δ4.97 (s,4H), 3.5 (bs,2H); $^{13}$C-nmr (deuteriomethyl sulfoxide): δ53.4, 107.2, 113.6, 118.3, 123.1, 127.8. Anal. Calcd. for $C_4H_6N_3O_7F_3S$: C, 16.17; H, 2.04; N, 14.14. Found: C, 16.58; H, 2.03; N, 13.85.

EXAMPLE 3

3,3-dinitroazetidinium trifluoromethanesulfonate (2.0 g, 0.0067 mole) was dissolved in 20 ml of water and neutralized with sodium bicarbonate (0.62 g, 0.0074 mole). The free base was extracted into chloroform (3×5 ml) and dried over sodium sulfate. The chloroform was removed under vacuum to quantitatively give the resultant product, 3,3-dinitroazetidine (0.98 g) as a colorless to light yellow oil.

Analysis $^1$H-nmr (deuteriochloroform): δ4.48 (s,4H), 2.18 (s,1H); $^{13}$C-nmr (deuteriochloroform): δ55.1, 111.57. Anal. Calcd. for $C_3H_5N_3O_4$: C, 24.50; H, 3.43; N, 28.57. Found: C, 24.50; H, 3.40; N, 28.58.

EXAMPLE 4

3,3-dinitroazetidinium trifluoromethanesulfonate (5.566 g) was dissolved in 50 ml of methanol and mixed with ammonium nitrate (1.5 g) in 20 ml of methanol. After about 1 minute, a precipitate began to form. The suspension was cooled and filtered to give 2.6 g of the resultant product, 3,3-dinitroazetidinium nitrate. The filtrate was reduced in volume to give an additional 1.0 g of the product (91% total yield).

Anal. Calcd. for $C_3H_6N_4O_7$: C, 17.15; H, 2.88; N, 26.61. Found: C, 17.18; H, 2.96; N, 24.65.

EXAMPLE 5

3,3-dinitroazetidinium trifluoromethanesulfonate (1.688 g) was dissolved in 5 ml of absolute ethanol and slowly added with stirring to ammonium 3,5-dinitro-1,2,4-triazolate (1.0 g) in 30 ml of absolute ethanol. A precipitate formed and was filtered. The filtrate was reduced in volume and refiltered through the original filter cake. The cake was washed with cold ethanol and air dried to give 1.42 g of the resultant product, 3,3-dinitroazetidinium 3,5-dinitro-1,2,4-trizolate (82% yield).

Anal. Calcd. for $C_4H_6N_8O_8$: C, 19.62; H, 1.98; N, 36.60. Found: C, 19.75; H, 2.05; N, 35.15.

EXAMPLE 6

3,3-Dinitroazetidine free base (2.0 g, 136 mmol) dissolved in methanol was added with stirring to 4,4',5,5'-tetranitro-2,2'-bi-imidazole dihydrate (2.38 g, 6.8 mmol) dissolved in warm water. The bright yellow precipitate was collected from the cooled suspension by filtration and air dried to give 3.90 g of the resultant product, di-(3,3-dinitroazetidinium) 4,4',5,5'-tetranitro-2,2'-bi-imidazolate (95% yield).

Anal. Calcd. for $C_{12}H_{12}N_{14}O_{16}$: C, 23.69; H, 1.99; N, 32.29. Found: C, 23.73; H, 2.07; N, 31.01.

EXAMPLE 7

3,3-Dinitroazetidine free base (1.0 g) was added to a solution of 2,4-dinitroimidazole (1.07 g) in 50 ml of warm acetonitrile. The solution was allowed to cool and the majority of the solvent evaporated. The remaining slurry was filtered and dried to give 1.98 g of the resultant product, 3,3-dinitroazetidinium 2,4-dinitroimidazolate (95% yield).

Anal. Calcd. for C$_6$H$_7$N$_7$O$_8$: C, 23.62; H, 2.31; N, 32.13. Found: C, 23.78; H, 2.39; N, 31.46.

EXAMPLE 8

Ammonium dinitramide (0.25 g) was dissolved in a few millimeters of water and loaded onto a Dowex 50-W H$^+$ form washed ion exchange column of approximately 20 ml volume. The column was eluted with three to four column volumes of water. The solution of dinitramidic acid was then neutralized with the free base 3,3-dinitroazetidine (0.29 g) and the water removed by rotary evaporation. The resulting product was recrystallized from a mixture of ethyl acetate and toluene to give 0.44 g of the resultant product 3,3-dinitroazetetidinium dinitramidate as a white powder (85% yield).

Anal. Calcd. for C$_3$H$_6$N$_6$O$_8$: C, 14.18; H, 2.38; N, 33.07. Found: C, 14.59; H, 2.45; N, 31.07.

EXAMPLE 9

3,3-Dinitroazetidine free base (1.0 g) was added to a solution of 5-nitro-1,2,4-triazol-3-onate (0.88 g) in 50 ml of warm methanol. The solution immediately turned to a lemon yellow color and a yellow solid began to precipitate. The solution was allowed to cool and the some of the methanol solvent was evaporated. The remaining slurry was filtered and dried to give 1.75 g of the resultant product, 3,3-dinitroazetetidinium 5-nitro-1,2,4-triazol-3-onate (93% yield).

Anal. Calcd. for C$_5$H$_7$N$_7$O$_7$: C, 21.67; H, 2.55; N, 35.38. Found: C, 21.72; H, 2.64; N, 35.02.

The physical properties of the various products of the examples are shown in Table 1. Impact sensitivity was measured on a Model 12 impact machine with a 2.5 kg drop weight. The spark test was with a 3-mil foil.

TABLE 1

| Salt from example | Melting Point (°C.) | Impact Sensitivity (cm) | Spark Test (J) | ΔH$_f$ (kcal/mole) | Density (g/cm$^3$) |
|---|---|---|---|---|---|
| #4 | 142 | 32 | 0.5 | −64 ± 2 | α 1.764 β 1.717 |
| #5 | 148 | 37 | 0.5 | +20 ± 2 | 1.694 |
| #6 | 154 | 71 | 1.3 | +5 ± 15 | — |
| #7 | 151 | 54 | 0.9 | −18 ± 12 | 1.656 |
| #8 | 138 | 14 | 1.1 | −8 ± 4 | 1.791 |
| #9 | 161 | 42 | 0.6 | −48 ± 1 | 1.757 |

EXAMPLE 10

Following the preparation of 3,3-dinitroazetidine as in example 3 and 3,3-dinitroazetidinium nitrate as in example 4, the 3,3-dinitroazetidinium nitrate was converted to 1,3,3-trinitroazetidine as follows. To acetic anhydride (1.50 g, 14.7 mmol) was added 0.030 g of 90% nitric acid and 0.026 g of anhydrous zinc chloride. To this mixture was added 3,3-dinitroazetidinium nitrate (1.0 g, 4.8 mmol). The resultant thick slurry was heated to 40° C. thereat yielding a resultant solution. The solution was allowed to cool to room temperature, drowned with water, and allowed to crystallize. The resultant product was filtered, washed with water and dried to yield 0.87 g of pure 1,3,3-trinitroazetidine. This material was spectrally identical to a sample of 1,3,3-trinitroazetidine prepared according to Archibald et al., J. Org. Chem., 55, 2920 (1990).

Although the present invention has been described with reference to specific details, it is not intended that such details should be regarded as limitations upon the scope of the invention, except as and to the extent that they are included in the accompanying claims.

What is claimed is:

1. 3,3-dinitroazetidine.

2. A process of preparing 3,3-dinitroazetidine comprising:
   reacting a mixture of 1-tertiarybutyl-3,3-dinitroazetidine and a chloroformate to form a 1-(R-substituted oxycarbonyl)-3,3-dinitroazetidine where R is an alkyl, aryl, or benzyl group;
   reacting said 1-(R-substituted oxycarbonyl)-3,3-dinitroazetidine and trifluoromethanesulfonic acid to form 3,3-dinitroazetidium trifluoromethanesulfonate; and,
   neutralizing said 3,3-dinitroazetidium trifluoromethanesulfonate with a base to form 3,3-dinitroazetidine.

3. The process of claim 2 wherein said 3,3-dinitroazetidinium trifluoromethanesulfonate is neutralized with sodium bicarbonate.

4. The process of claim 2 wherein said chloroformate is benzyl chloroformate.

5. A salt of 3,3-dinitroazetidine.

6. The salt of claim 5 including an anion selected from the group consisting of nitrate, 3,5-dinitro-1,2,4-triazolate, 4,4',5,5'-tetranitro-2,2'-bi-imidazolate, picrate, trinitromethylate, 5,5'-dinitro-3,3'-bi(1,2,4-bitriazolate), trinitroimidazolate, 3,5-dinitropyrazolate, 4,5-dinitroimidazolate and nitrotetrazolate.

7. The salt of claim 5 wherein the salt is 3,3-dinitroazetidinium nitrate.

8. The salt of claim 5 wherein the salt is 3,3-dinitroazetidinium 3,5-dinitro-1,2,4-triazolate.

9. The salt of claim 5 wherein the salt is di-(3,3-dinitroazetidinium) 4,4',5,5'-tetranitro-2,2'-bi-imidazolate.

10. The salt of claim 5 wherein the salt is 3,3-dinitroazetidinium dinitramidate.

11. The salt of claim 5 wherein the salt is 3,3-dinitroazetidinium 2,4-dinitroimidazolate.

12. The salt of claim 5 wherein the salt is 3,3-dinitroazetidinium 5-nitro-1,2,4-triazol-3-onate.

* * * * *